United States Patent [19]

Taillandier et al.

[11] 4,032,660
[45] June 28, 1977

[54] ACETOXIME DERIVATIVES AND PROCESS FOR PREPARING THE SAME

[75] Inventors: Georges Marcel Taillandier; Jean-Louis Alain Benoit-Guyod, both of Grenoble; André Louis Boucherle, Corenc-Montfleury; Pierre Luc Eymard, Fontaine; Madeleine Broll, Grenoble, all of France

[73] Assignee: Labaz, Paris, France

[22] Filed: June 5, 1975

[21] Appl. No.: 584,176

[30] Foreign Application Priority Data

June 25, 1974 France .............................. 74.22033

[52] U.S. Cl. .............................. 424/327; 260/566 A
[51] Int. Cl.² ...................................... A61K 31/15
[58] Field of Search ................ 424/327; 260/566 A

[56] References Cited

UNITED STATES PATENTS

| | | | |
|---|---|---|---|
| 3,224,873 | 12/1965 | Swanson | 75/101 |
| 3,346,523 | 10/1967 | Wiese | 260/566 X |
| 3,437,454 | 4/1969 | Shaw | 260/566 X |
| 3,794,719 | 2/1974 | Lowenhaupt et al. | 260/566 X |

Primary Examiner—Frederick E. Waddell
Attorney, Agent, or Firm—Mason, Kolehmainen, Rathburn & Wyss

[57] ABSTRACT

Acetoxime derivatives of formula:

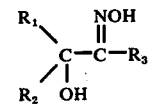

wherein $R_1$, $R_2$ and $R_3$, which may be the same or different, each represent a branched- or straight-chain alkyl radical having from 1 to 4 carbon atoms or $R_1$ and $R_2$, when they are taken together, represent with the carbon atom to which they are attached, a cyclohexyl group, are useful for treating disturbances of the mental functions including anxiety and as anticonvulsants.

5 Claims, No Drawings

ACETOXIME DERIVATIVES AND PROCESS FOR PREPARING THE SAME

This invention relates to acetoxime derivatives having pharmacological activity, to a process for preparing them and to pharmaceutical and veterinary compositions containing them.

The acetoxime derivatives with which the invention of concerned are represented by the general formula:

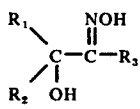

wherein $R_1$, $R_2$ and $R_3$, which may be the same or different, each represent a branched-or straight-chain lower alkyl radical having from 1 to 4 carbon atoms or $R_1$ and $R_2$, when they are taken together, represent with the carbon atom to which they are attached, a cyclohexyl group.

The invention is also concerned with pharmaceutical or veterinary compositions comprising as essential active ingredient at least one of the compounds represented by formula I in association with a pharmaceutical carrier or excipient therefor.

Another object of the invention is to provide a process for preparing pharmaceutical or veterinary compositions whereby at least one acetoxime derivative of formula I is associated with a pharmaceutical carrier or excipient therefor.

As demonstrated further on in detail, it has been found that the acetoxime derivatives of the invention are endowed with pharmacological properties which are likely to render them useful as tranquillizers, thymoanaleptics, myorelaxants, anticonvulsants and sedative agents exerting their effect on the central nervous system.

Another object of the invention is therefore to provide a method for treating disturbances of the mental functions including anxiety as well as convulsive states of the central nervous system especially epilepsy.

The daily therapeutic dose will be preferably from 200 to 1000 mg of active ingredient administered to a human weighing 60 kg.

The compounds of formula I are either products specifically cited in prior publications or products only included within the scope of general formulae previously published. In this connection, C.R. Acad. Sci. 176, 516–518 (1923) and U.S. Pat. No. 3,346,523 can be cited.

However no pharmacological property is described or even mentioned in these references with respect to the compounds of formula I.

The compounds of formula I can be prepared by heating in an appropriate solvent such as an alcohol for example ethanol and in the presence of an acid acceptor such as for example pyridine, a ketone of the general formula:

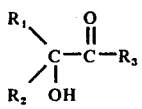

wherein, $R_1$, $R_2$ and $R_3$ have the same meaning as in formula I, with hydroxylamine hydrochloride or sulphate, to obtain the required acetoxime derivative of formula I.

The compound of formula II wherein $R_1$, $R_2$ and $R_3$, which are identical each represent methyl is a known compound having been described in Berichte D. ch. G. Sept. 16, 1922 p. 2903. Similarly, the compounds of formula II wherein $R_1$ represents tert butyl and $R_2$ represents methyl or $R_1$ and $R_2$, which are identical each represent ethyl or n-propyl or $R_1$ and $R_2$ when they are taken together represent with the carbon atom to which they are attached, a cyclohexyl radical and $R_3$ represents methyl are also known compounds having been published in C.R. Acad. Aci., 176, 516–518 (1923).

The other hydroxyketones of formula II may be prepared following known processes in particular by hydrolysing the corresponding ethinylcarbinol derivatives in the presence of mercury acid sulphate as described in the above cited reference from C.R. Acad. Sci. These ethinylcarbinol derivatives can be obtained by condensing ketonic derivatives with acetylenic derivatives in the presence of naphthalene and sodium as published in Bull. Soc. Chim. France 1960, 2, 354–359.

The ketone and acetylenic derivatives which are necessary for preparing the required compounds of formula II are all known compounds.

As mentioned above the acetoxime derivatives of the invention have been found to possess a wide range of psychotropic properties and, in particular, tranquillizing and thymoanaleptic properties including anxiolytic and antidepressant activities as well as anticonvulsant, myorelaxant activities and, at higher doses, a sedative action on the central nervous system. Furthermore, the compounds of the invention are completely devoid of any neuroleptic properties.

These pharmacological properties, taken as a whole, are likely to render the compounds of the invention useful in the treatment of mental disorders requiring or not, a mild sedative action.

It is known that a patient in a state of deep depression and who is being treated with antidepressants can manifest anxiety reactions when the depression begins to lift and when he becomes aware of his depressed condition.

This phenomenon is reported by RECH and MOORE in "An Introduction to Psychopharmacology" p. 337 (1971) where it is said:

"There are reports of attempts at suicide during the initial stages of treatment with antidepressant drugs . . . when the patient began to show objective signs of improvement. This paradoxical phenomenon during what appeared to be successful treatment has been explained as an increase in psychomotor drive to the extent that the patient is able to implement a suicidal wish, but still suffers from a significant degree of depressive effect".

With a view to preventing this anxious reaction when antidepressants are administered, the practician has recourse to a tranquillizer of the anxiolytic type which he associates with the antidepressant employed.

Moreover, as anxiety is involved to a greater or lesser extent in all cases of depression, any agent that relieves the contributing tension will presumably afford some relief. For this reason, many therapeutic compositions associate both antidepressant and tranquillizing agents as most of the antidepressants used at present do not possess tranquillizing properties.

The essential value of the compounds of the invention lies in the fact that they present, in one and the same molecule of very slight toxicity, the twofold advantage of an antidepressant action combined with a tranquillizing effect of the anxiolytic type. This advantage enables the commonly found association of an antidepressant with a tranquillizer in one single medicament to be avoided. It also makes it possible to avoid the administration of an antidepressant and a tranquillizer as two separate medicaments.

The advantage of the compounds of the invention lies in the fact that neither antidepressant properties nor their tranquillizing properties are exhibited to the same degree of intensity as that which characterizes the individual action of the antidepressants as such and the tranquillizers as such.

The compounds of the invention combine these two properties so that the mild tranquillizing effect facilitates the antidepressant action of these compounds. This is because of the intervention of anxiety in the behaviour of the depressed patient as mentioned above. Hence the patient is enabled to benefit to the maximum from the two properties which the compounds of the invention possess without being exposed to the risk of experiencing the undesirable side effects which so often accompany the administration of antidepressants and tranquillizers as separate medicaments.

Amongst the antidepressants possessing a tranquillizing factor, certain tricyclic antidepressant agents may be cited. However, these compounds provoke to a certain degree side-effects of an anti-cholinergic nature such as dryness of the mouth, difficulties in optical accommodation, sweating and tachycardia. These undesirable side-effects can be avoided with the compounds of the invention at the doses employed to obtain an antidepressant effect combined with a tranquillizing action.

Moreover, in the treatment of epileptic patients with tricyclic antidepressants, it is generally necessary to increase the dose of the anticonvulsant. The disadvantage can also be avoided with the compounds of the invention since the latter possess, at tranquillizing and antidepressant doses, an anticonvulsant action of appreciable intensity.

The tranquillizing effect which has been observed with the compounds of the invention enables the latter to be generally classified in the category of the minor tranquillizers, i.e. amongst the psychotropic compounds which possess an anticonvulsant, an anxiolytic and a myorelaxant action and are devoid of any cataleptic activity. Furthermore, these properties are exhibited at doses which always give a very favourable ratio with the neurotoxic dose 50 discussed below. The compounds of the invention may thus be considered comparable with compounds of the benzodiazepine type. Moreover, the tranquillizing action is already apparent at non-sedative doses which constitutes an advantage when no sedation is required.

Like pain, the various types of anxiety are numerous and constitute one of the most widespread disorders to which man is subject. For this reason, it is very difficult for the doctor to choose amongst the various tranquilizing drugs at his disposal, that which will be effective for the case under treatment.

When faced with a case of anxiety, the psychiatrist is often obliged to feel his way by trying several tranquilizing drugs one after the other until he discovers the most suitable medicament.

As regards this aspect of the question, the compounds of the invention will constitute valuable additions to the therapeutic arsenal at the disposal of the doctor and, if necessary, will provide useful replacement medication for a drug which has become ineffective for any reason such as, for example, a change in the state of the patient or habituation.

The compounds of the invention which were found to possess particularly useful tranquillizing properties were:

3-ethyl-3-hydroxy-2-hexanone oxime
3-n-propyl-3-hydroxy-2-hexanone oxime and
3-n-butyl-3-hydroxy-2-heptanone oxime Pharmacological trials have been undertaken with a view to determining the toxicity of the compounds of the invention as well as the presence of the various properties which, taken together, are capable of rendering the said compounds useful as tranquillizers, thymoanaleptics, anticonvulsants, myorelaxants and sedative agents exerting their effect on central nervous system.

1. ACUTE TOXICITY

The acute toxicity was determined on mice of the Swiss strain. To this end, the mice were divided into batches of five. Each batch of animals was then given an intraperitoneal dose of the compound to be studied dissolved in neutralised olive oil. Dosage was arranged so that each batch received a higher dose than the preceding batch. The maximum tolerated dose (M.T.D.) was thus determined i.e. the highest dose that the animals could receive without any deaths occurring.

The following results were registered with the compounds of the invention listed hereunder:

3-Ethyl-3-hydroxy-2-pentanone oxime (Compound A)
3-Methyl-3-hydroxy-2-hexanone oxime (Compound B)
3-Ethyl-3-hydroxy-2-hexanone oxime (Compound C)
3-n-Propyl-3-hydroxy-2-hexanone oxime (Compound D)
3-n-Butyl-3-hydroxy-2-heptanone oxime (Compound E)
5-n-Propyl-5-hydroxy-4-octanone oxime (Compound F)
1-Acetyl-1-cyclohexanol oxime (Compound G)

| Compound | M.T.D. in mg/kg |
| --- | --- |
| A | 600 |
| B | 400 |
| C | 600 |
| D | 500 |
| E | 600 |
| F | 700 |
| G | 600 |

2. HYPNOTIC PROPERTIES

The hypnotic properties of the compounds of the invention were demonstrated by studying posture reflex.

Male mice of the $OF_1$ strain, weighing about 22 g., were divided into batches of 10. The animals of each batch were given an intraperitoneal dose of the compound to be studied so that each batch received a higher dose than the preceding batch.

The numbers of animals which lost the reflex at 30 minutes after administration were noted.

In this way, the $HD_{50}$ was determined, i.e. the dose of the compound under study which caused 50% of the animals to lose the posture reflex at 30 minutes after administration.

The following results were obtained for compounds of the invention:

| Compound | $HD_{50}$ in mg/kg |
|---|---|
| A | 250 |
| B | 350 |
| C | 240 |
| D | 250 |
| E | 350 |
| F | 300 |
| G | 500 |

3. ACTION ON BEHAVIOUR a. Determination of the neurotoxic dose 50

The test used was that known as the rotated test described by BOISSIER (Therapie 1958, XIII, pp 107–1118).

This test aimed at enabling the animals' ability to coordinate their movements to be evaluated.

It was carried out on batches of 10 mice each weighing about 22 g. The compound to be tested was administered by intraperitoneal route to the animals of each batch so that each batch received a higher dose than that given to the preceding batch.

Thirty minutes after administration, the mice were placed for 2 minutes on a wooden roller of 4.8 cm. diameter turning at the rate of four revolutions per minute. The roller had a rough surface to prevent the animals from slipping.

By this means, the neurotoxic dose $50(NTD_{50})$ could be determined, i.e. the dose of the compound with which one half of the animals could not stay on the roller during the period of time fixed as the reference period.

The value of this test is twofold. Failure on the part of the animals gives a very early indication of the slightest damage to the neuromuscular functions which cannot be discerned by any other means. Secondly, this test serves as an element of comparison for drawing up index figures involving the results obtained with other behaviour tests.

The following results were recorded with compounds of the invention:

| Compound | $NTD_{50}$ in mg/kg |
|---|---|
| B | 150 |
| C | 120 |
| D | 110 |
| E | 180 |
| F | 150 |
| G | 225 | b. Action on Spontaneous Motricity

The purpose of this test was to determine the dose of the compounds of the invention which were capable of increasing or decreasing motricity, i.e. one of the behaviour factors of the animal in its usual environment.

Mice were divided into several identical batches comprising from 10 to 20 animals each. The equipment consisted of a double electromagnetic apparatus on one side of which was placed a cage containing the control group of animals while on the other side there was placed a cage containing the same number of mice previously treated by intraperitoneal route with a compound of the invention. The dose of the compound to be studied was calculated so that each batch of animals received a higher dose than the preceding batch.

As soon as the compound under study was administered all the movements of the animals were registered through the disturbances they caused in the magnetic field and then added up for each period of time. In this way, the significant dose was determined, i.e. the dose of the compound under study which is required to diminish by at least 30% the motricity of the treated animals as compared to the controls. It was found that this significant dose was effective 30 minutes after administration of the compound under study.

With regard to, for example, Compounds C and D, this significant dose was found to be 75 and 100 mg/kg respectively.

4. TRANQUILLIZING PROPERTIES

Anxiolytic Action

The anxiolytic action was demonstrated by means of the four plates test of BOISSIER (European J. Pharmacol. 1968, 4,145–151)

Mice were divided into four identical batches of 10 to 20 animals of which two batches were the control batches. The equipment used consisted of an apparatus on which were mounted four metal plates.

These plates were connected alternatively to positive and negative sources of electric current so that, when the current was switched on, any animal passing over the plates received a shock through contact with two opposing electric poles. Each mouse was placed individually on the apparatus.

The first batch of control animals was allowed to explore the plates without any current and the second batch of controls with the current switched on. It was observed that the untreated controls of the second batch quickly refused to explore the electrified plates out of fear of a shock.

The third and four batches of animals were given different doses of the compound to be tested by intraperitoneal route. No animal was used twice, each mouse being allowed to explore either the electrified plates or the non-electrified plates. It was observed that the treated animals, under the influence of the anxiolytic action of the compound to be tested, were markedly less afraid than the controls.

This test made it possible to calculate the first dose of compound required to achieve a significant increase in the number of electrified plates crossed while the same number of non-electrified plates were crossed in order to distinguish an anxiolytic action from a possible alteration of spontaneous motricity.

Under these circumstances, it was found that the effective dose (ED) of the compounds of the invention is as follows:

| Compound | ED in mg/kg |
| --- | --- |
| A | 100 |
| B | 150 |
| C | 75 |
| D | 50 |
| E | >150 |
| F | 150 |
| G | 150 |

When comparing the ED obtained in this test with the M.T.D. given hereabove, it is observed that this M.T.D. is from 2.5 to 10 times superior to the anxiolytic ED in question.

These figures, indicate a very wide safety margin between the anxiolytic ED and the $LD_{50}$, this latter dose itself, of course, superior to the M.T.D.

5. NEUROLEPTIC PROPERTIES

In the rat, all the catalepsy tests (crossing of homolateral paws, four corks test, parallel bars test) carried out with the compounds of the invention gave negative results.

Similarly, tests were performed to determine whether the compounds of the invention inhibit amphetamine-induced toxicity in a group. To this end, mice were divided into batches of 10. The animals of each group which were maintained in a cage received and hypnotic dose 50 of the compound to be studied by intraperitoneal route, 15 minutes before the injection of 20 mg/kg of amphetamine sulphate by intraperitoneal route.

It was observed that the compounds of the invention do not inhibit amphetamine-induced toxicity in a group even at hypnotic doses, which confirms the absence of neuroleptic properties.

6. THYMOANALEPTIC (ANTIDEPRESSANT) ACTIVITY

Antireserpine Action

The antidepressants antagonize or delay the sedative action of reserpine as measured by means of ptosis and catatonia in rats.

An intraperitoneal dose of 50 mg/kg of the compound to be studied was given to batches of 5 male rats of the $CF_1$ strain weighing an average of 300 g. Thirty minutes later a dose of 3 mg/kg of reserpine was given by the same route. Ptosis and catatonia were noted 3 hours after administration of the reserpine. An identical test was carried out with control animals which were given reserpine but none of the compounds of the invention.

Ptosis was evaluated for each eye in accordance with the following scale:

0 : eyelids open
1 : eyelids ¼ closed
2 : eyelids ½ closed
3 : eyelids ¾ closed
4 : eyelids completely closed Thus, for example, if an animal had a ptosis of 1 for one eye and 2 for the other, it was given the score of 1.5.

The results obtained for the compounds of the invention are given hereunder, each figure representing the average of 10 tests (5 animals of which both eyes were examined).

Catatonia was evaluated by putting the front paws of the animal on a horizontally stretched wire fixed at 15 cm from the ground. The catatonic animals were those which maintained the position so given for at least 20 seconds. Each animal which maintained the position so given received the score of 1 and the score of 0 if it failed to maintain the position in question.

The results obtained with compounds of the invention are given hereunder, each figure representing the average obtained in five tests.

|  | Ptosis | Catatonia |
| --- | --- | --- |
| Controls | 3.7 | 3 |
| Compound |  |  |
| A | 2.1 | 0 |
| B | 3.2 | 1 |
| C | 3.— | 0 |
| D | 2.8 | 0 |
| E | 3.— | 0 |
| F | 3.— | 0 |
| G | 3.— | 0 |

7. ANTICONVULSANT ACTION a. Pentylenetetrazol-induced Seizure

The purpose of this test which was carried out on mice was to determine whether the compounds of the invention, when given preventively by intraperitoneal route, were capable at certain doses of protecting some of the animals against the epileptic seizure produced by predetermined dose of pentylenetetrazol which would be 100% fatal in the absence of the compound.

The test was carried out on batches of 10 male mice. Each batch of animals received an intraperitoneal dose of the compound to be studied so that each batch received a higher dose than the preceding batch. Fifteen minutes after administration, the animals were each given 125 mg/kg of pentylenetetrazol by intraperitoneal route and the number of deaths was noted 3 hours after administration of the pentylenetetrazol.

The $ED_{50}$, i.e. the dose which protected 50% of the animals against death, was found to be as follows with compounds of the invention:

| Compound | $ED_{50}$ (in mg/kg) |
| --- | --- |
| A | 50 |
| B | 80 |
| C | 60 |
| D | 60 |
| E | 100 |
| F | 90 |
| G | 150 |

The efficacy index of the compounds was also calculated by comparing the $ED_{50}$ found in this test with the dose required to obtain a hypnotic effect in 50% of the animals. This latter value is indicated by the symbol $HD_{50}$ or hypnotic dose 50 and the efficacy index by the fraction: ($HD_{50}/ED_{50}$)

The efficacy indices obtained for compounds of the invention in comparison with phenobarbital are the following:

| Compound | Index |
| --- | --- |
| A | 5 |
| B | 4.4 |
| C | 4 |
| D | 4.2 |

| Compound | Index |
|---|---|
| E | 3.5 |
| F | 3.3 |
| G | 3.3 |
| Phenobarbital | 3.3 |

These results show that when no sedation of the central nervous system is required, the compounds of the invention are at least as advantageous as phenobarbital and generally more advantageous than this latter compound with regard to the safety margin between the anticonvulsant dose and the hypnotic dose. Furthermore, unlike phenobarbital the compounds of the invention posses antidepressant properties.

Another efficacy index was also drawn up by comparing the $NTD_{50}$ with the $ED_{50}$ obtained in the test described hereabove, namely the dose required to obtain an anticonvulsant action in 50% of the treated animals in comparison with the controls.

Such an index is expressed by the ratio ($NTD_{50}/ED_{50}$)

The following indices were registered with compounds of the invention:

| Compound | Index |
|---|---|
| B | 1.9 |
| C | 2 |
| D | 1.8 |
| E | 1.8 |
| F | 1.7 |
| G | 1.5 |

These figures indicate that there exists, in this test, an appreciable safety margin between the anticonvulsant dose and the dose which provokes disturbances in the neuromuscular functions.

b. Maximum Electroshock Seizure

This seizure is characterized in the mouse by extension of the back paws for 5 to 10 seconds. The extension is similar to that observed during the tonicoclonic seizures provoked by chemical convulsants such as pentylenetetrazol or strychnine.

The test was carried out on batches of 10 mice. On the day preceding the test the animals received a convulsant electroshock (30 volts, 50 periods for 0.4 second) in order to select the sensitive mice. On the next day various doses of the compound to be studied were administered by intraperitoneal route to the animals so selected so that each batch of mice received a higher dose than the preceding batch. Fifteen minutes later, each animal received an electric shock of 60 volts, 50 periods for 0.4 second. The percentage of mice protected against tonic seizures was noted and the $ED_{50}$ was calculated i.e. the dose of the compound under study required to protect 50% of the animals against tonic seizures.

The following results were obtained with compounds of the invention:

| Compound | $ED_{50}$ in mg/kg |
|---|---|
| A | 250 |
| B | 270 |
| C | 200 |
| D | 200 |
| E | 300 |
| F | >200 |
| G | 200 |

8. MYORELAXANT PROPERTIES

The myorelaxant properties of the compounds of the invention were determined by the traction test described by COURVOISIER (Psychotropic Drugs, Milan 1957, pp 373–391) and at the same time the anti-strychnine properties of these compounds were verified.

a. Traction Test

This test enables sense of balance as well as muscular tonus and strength to be evaluated.

The test was carried out on groups of 10 male mice of the $OF_1$ strain weighing about 22 g. It consisted in suspending the mice by the front paws to a horizontally stretched wire. Note was first taken of the time required by a group of control animals to effect recovery, i.e. to place at least one of their back paws on the wire.

Each batch of animals to be treated was then given an intraperitoneal dose of the compound to be studied so that each batch received a higher dose than the preceding batch. Note was then taken of the number of animals which had lost the traction reflex 30 minutes after administration of the compound and the $ED_{50}$ was calculated, i.e. the dose of the compound under study which causes loss of the reflex in 50% of the animals.

Under these conditions; the $ED_{50}$ for compound of the invention was found to be as follows:

| Compound | $ED_{50}$ in mg/kg |
|---|---|
| A | 130 |
| B | 200 |
| C | 100 |
| D | 110 |
| E | 150 |
| F | 200 |
| G | 250 |

In order to obtain an activity index figure, a comparison was made between the $NTD_{50}$ and the $ED_{50}$ obtained with the traction test with respect to compounds of the invention and a well-known myorelaxant agent namely mephenesin. This index figure is represented by the ratio ($NTD_{50}/ED_{50}$)

| Compound | Index |
|---|---|
| B | 0.7 |
| C | 1.2 |
| D | 1.— |
| E | 1.2 |
| F | 0.7 |
| G | 0.9 |
| Mephenesin | 0.4 (= 100/250) |

These figures show a favourable activity index for the compounds of the invention as compared with the activity index of the known myorelaxant.

It is seen, in fact, in the case of the compounds of the invention, that the myorelaxant dose is much further removed from the neurotoxic dose then in the case of mephenesin.

b. Antagonism to Strychnine

Batches of 10 male mice were treated by intraperitoneal route with 100 mg/kg of a compound of the invention. Fifteen minutes later, the animals were given at a rate of 0.5 ml/min a perfusion in the caudal vein of an aqueous solution containing 0.05 mg/ml of strychnine sulphate.

Note was taken of the average time when tonic seizures appeared which was expressed in seconds.

The same test was performed with control animals which did not receive any compound of the invention but only strychnine.

The following results were registered:

| Compound | Time in seconds |
|---|---|
| Controls | 49.6 |
| A | 56.8 |
| B | 57.8 |
| C | 55.2 |
| D | 54.— |
| E | 56.4 |
| F | 51.2 |
| G | 52.— |

It will be appreciated that for therapeutic use the compounds of the invention will normally be administered in the form of a pharmaceutical or veterinary composition in a dosage unit form appropriate to the required mode of administration, the composition comprising as active ingredient at least one compound of the invention in association with a pharmaceutical carrier or excipient therefor.

For oral administration, the composition may take the form of, for example a coated or uncoated tablet, a hard or soft gelatin capsule, a suspension or a syrup. The composition may alternatively take the form of a suppository for rectal administration, or of a solution or suspension for parenteral administration.

When in dosage unit form, the composition may contain from 50 to 500 mg, preferably 100 to 250 mg, of the active ingredient per dosage unit for oral administration and from 50 to 500 mg of the active ingredient per dosage unit for rectal administration.

The compositions of the invention will be prepared by associating at least one of the compounds of formula I with at least one appropriate carrier or excipient therefor.

Examples of suitable carriers or excipients are talc, magnesium stearate, milk sugar, saccharose, carboxymethylcellulose, starches, kaolin, levilite, cocoa butter.

The following Examples illustrate the preparation of the compounds of the invention together with therapeutic compositions containing them:

EXAMPLE 1

Preparation of 3-ethyl-3-hydroxy-2-hexanone oxime

In a flask fitted with a condenser, a mixture of 7.2 g (0.05 mol) of 3-ethyl-3-hydroxy-2-hexanone, 6.95 g (0.1 mol) of hydroxylamine hydrochloride, 75 ml of ethanol and 7.5 ml of pyridine were heated for 2 hours on a water-bath. The alcohol was eliminated by evaporating under vacuum and 75 ml of distilled water were added to the residue so obtained.

The aqueous solution was cooled and then extracted with ether. The ethereal phase was dried over anhydrous sodium sulphate and evaporated. The oxime which crystallized was then purified from recrystallization in warm octane. In this manner, 5.53 g of 3-ethyl-3-hydroxy-2-hexanone oxime were obtained which represents a yield of 70% when compared to the starting hydroxyketone. M.P. 59° C Following the same procedure as that described above but using the appropriate starting-products, the following compounds were prepared:

| Compound | Melting point ° C |
|---|---|
| 3-Ethyl-3-hydroxy-2-pentanone oxime (yield : 71%) | 51 |
| 3-Methyl-3-hydroxy-2-hexanone oxime (yield : 56%) | 56.4 |
| 3-n-propyl-3-hydroxy-2-hexanone oxime (yield : 85%) | 66.8 |
| 3-n-Butyl-3-hydroxy-2-heptanone oxime (yield : 74%) | 51.5 |
| 5-n-Propyl-5-hydroxy-4-octanone oxime (yield : 20%) | 68 |
| 1-Acetyl-1-cyclohexanol oxime (yield : 42%) | 106.5 |

EXAMPLE 2

Soft-gelatin capsules corresponding to the following formulation were prepared by known pharmaceutical techniques:

| Ingredient | mg/per capsule |
|---|---|
| 3-Ethyl-3-hydroxy-2-hexanone oxime | 150 |
| Talc | 15 |
| Magnesium stearate | 2 |
| | 167 |

We claim:

1. A method for treating anxiety and convulsive states of the central nervous system in a subject in need of such treatment comprising administering to the said subject 200 to 1000 milligrams per 60 kilograms of body weight per day of at least one acetoxime derivative of the formula:

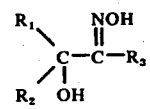

wherein $R_1$, $R_2$ and $R_3$, which may be the same or different, each represent a branched-or straight-chain alkyl group having from 1 to 4 carbon atoms or $R_1$ and $R_2$, when they are taken together, represent with the carbon atom to which they are attached, a cyclohexyl group.

2. A method according to claim 1 comprising administering 3-ethyl-3-hydroxy-2-hexanone oxime.

3. A method according to claim 1 comprising administering 3-n-propyl-3-hydroxy-2-hexanone oxime.

4. A method according to claim 1 comprising administering 3-n-butyl-3-hydroxy-2-heptanone oxime.

5. A method according to claim 1 wherein the convulsive states are epileptic.

* * * * *